United States Patent [19]

Kuznitz et al.

[11] Patent Number: 5,198,218
[45] Date of Patent: Mar. 30, 1993

[54] CLEAR COSMETIC STICKS WITH COMPATIBLE FRAGRANCE COMPONENTS

[75] Inventors: Matthew Kuznitz, Branford; David A. Brewster, Shelton; Joseph R. Faryniarz, Oxford; Lewis Cancro, Trumbull, all of Conn.; Hifzur R. Ansari, Old Tappan, N.J.

[73] Assignee: Chesebrough-Pond's USA Co., Division of Conopco, Inc., Greenwich, Conn.

[21] Appl. No.: 850,185

[22] Filed: Mar. 11, 1992

Related U.S. Application Data

[62] Division of Ser. No. 652,856, Feb. 8, 1991, Pat. No. 5,114,717.

[51] Int. Cl.$^5$ ................................ A61K 7/00
[52] U.S. Cl. .................. 424/401; 252/134; 252/315.4; 424/47; 424/65; 424/66; 424/68; 424/DIG. 5; 514/944
[58] Field of Search ............ 424/66, 68, 401, DIG. 5, 424/65, 47; 252/134, 315.4; 514/944

[56] References Cited

U.S. PATENT DOCUMENTS

| | | | |
|---|---|---|---|
| 2,900,306 | 8/1959 | Slater | 424/65 |
| 3,579,465 | 5/1971 | Schmolka | 252/315.1 |
| 3,740,421 | 6/1973 | Schmolka | 424/65 |
| 4,217,250 | 8/1980 | Holzner | 512/2 |
| 4,226,889 | 10/1980 | Yuhas | 424/59 |
| 4,268,498 | 5/1981 | Gedeon et al. | 424/59 |
| 4,278,658 | 7/1981 | Hooper et al. | 424/65 |
| 4,290,904 | 9/1981 | Poper et al. | 252/118 |
| 4,478,853 | 10/1984 | Chaussee | 514/772 |
| 4,565,693 | 1/1986 | Marschner | 424/67 |
| 4,702,916 | 10/1987 | Geria | 424/400 |
| 4,759,924 | 7/1988 | Luebbe et al. | 424/42 |
| 4,797,273 | 1/1989 | Linn et al. | 424/59 |
| 4,906,454 | 3/1990 | Melanson et al. | 424/47 |
| 4,944,937 | 7/1990 | McCall | 424/65 |
| 4,948,578 | 8/1990 | Burger et al. | 424/68 |
| 4,952,559 | 8/1990 | Login et al. | 512/10 |
| 5,011,681 | 4/1991 | Ciotti et al. | 252/174.15 |

FOREIGN PATENT DOCUMENTS 0137173  4/1985  European Pat. Off. .
0450597  10/1991  European Pat. Off. .

OTHER PUBLICATIONS

Ban Clear Solid Deodorant-xeroxed copies of product package.
"Applications of Pluronic ® Polyols in the Cosmetic Industry", Schmolka; American Perfumer and Cosmetics, vol. 82, Jul., 1967; pp. 25-30.
BASF Bulletin (1987), Pluronic ® & Tetronic ® Block Copolymer Surfactants.

Primary Examiner—Thurman K. Page
Assistant Examiner—Robert H. Harrison
Attorney, Agent, or Firm—Milton L. Honig

[57] ABSTRACT

A clear gel composition is provided which includes a polyhydric alcohol, a soap, an alkoxylate copolymer and a fragrance. For purposes of maintaining clarity, the fragrance will contain at most 25% of total ester compounds by weight of the fragrance.

12 Claims, No Drawings

CLEAR COSMETIC STICKS WITH COMPATIBLE FRAGRANCE COMPONENTS

This is a divisional application of Ser. No. 07/652,856 filed Feb. 8, 1991, now U.S. Pat. No. 5,114,717, issued May 19, 1992.

FIELD OF THE INVENTION

The invention relates to cosmetic compositions in the form of sticks having improved long-term clarity stability.

THE RELATED ART

Cosmetic compositions in stick form are well-known. These compositions may be employed as deodorants, antiperspirants, lipsticks and the like. Efforts have been made in the art to provide such compositions with improved clarity for aesthetic purposes.

U.S. Pat. No. 4,759,924 (Luebbe et al) discloses a transparent soap gel stick stated to possess good cosmetics as well as clarity. Deodorant formulas are described therein containing a polyhydric alcohol, soap, an ethyoxylated-propoxylated fatty alcohol, a fragrance and a deodorant active, such as triclosan, in an aqueous carrier. Similar compositions are reported in U.S. Pat. No. 4,504,465 (Sampson et al) and U.S. Pat. No. 4,617,185 (DiPietro).

Soap gel technology to achieve solid sticks has also been employed in U.S. Pat. No. 4,226,889 (Yuhas). Therein is reported an aqueous sodium stearate-water vehicle delivering an active ingredient for deposit on human skin. Among the actives are bacteriostats, fungistats, pigments, dyes, perfumes, emollients, humectants, ultraviolet absorbers, talc and insect repellants.

U.S. Pat. No. 4,702,916 (Geria) describes an analgesic stick comprising a delivery system of alcohol, soap, water, fragrance and a variety of analgesic agents.

U.S. Pat. No. 3,579,465 (Schmolka) discloses preparation of transparent ringing organic polymer gels structured through use of a polyoxyethylene-polyoxypropylene glycol adduct of ethylene diamine. Deodorant actives, astringents and pesticides are said to be includable within the gel structure.

U.S. Pat. No. 3,740,421 (Schmolka) reports formation of gels through use of polyoxyethylene-polyoxypropylene block polymers providing transparent products which may incorporate antiperspirant, astringent, antiseptic and other actives.

U.S. Pat. No. 2,900,306 (Slater) is concerned with formulation of frozen colognes. Among the components required to form stick products are a solid alcohol base having dispersed therein a minor amount of a water-soluble soap. Deodorant sticks are described therein with a major amount of alcohol solidified by a minor amount of sodium stearate, a deodorant and a minor amount of a lower alkylolamine soap.

EP 0 137 173 (Graham) describes a deodorant formulation containing a lower alcohol, water and amino alkanol, such as 2-amino-2-methylpropan-1-ol. Amino alcohols were said to provide improved deodorancy and clear formulations.

U.S. Pat. No. 4,948,578 (Burger et al) describes an antiperspirant composition in the form of a transparent stick comprising a mixture of aluminum chlorhydrate, ethoxylated nonionic surfactant, a volatile silicone, an emollient oil and water.

Beyond the technical literature, there is also in public use a wide variety of translucent deodorant sticks. For instance, a typical consumer product such as Power Stick ® lists on the package as ingredients: propylene glycol, water, sodium stearate, lauramide DEA, fragrance, triclosan, hydroxyethylcellulose and colorants.

A problem with the known art is that the products which upon manufacture are relatively transparent will over time lose a substantial amount of clarity. This is especially evident with soap structured gels. Improvements are, therefore, necessary to achieve long-term clarity stability.

Accordingly, it is an object of the present invention to provide a cosmetic stick having superior consumer performance properties.

Another object of the present invention is to provide a cosmetic stick having improved aesthetic properties.

A further object of the present invention is to provide a cosmetic stick exhibiting long-term clarity.

A still further object of the present invention is to provide a cosmetic stick for use as a deodorant with the improved property of better clarity stability.

These and other objects of the present invention will become more apparent by consideration of the following summary, detailed description and examples.

SUMMARY OF THE INVENTION

A clear gel composition is provided comprising:
(i) from about 10 to about 90% of a polyhydric alcohol having from 2 to 6 carbon atoms and from 2 to 6 hydroxyl groups;
(ii) from about 1 to about 40% of a soap;
(iii) from about 1 to about 40% of an alkoxylate copolymer having the following formula:

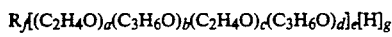

$$R_f[(C_2H_4O)_a(C_3H_6O)_b(C_2H_4O)_c(C_3H_6O)_d]_e[H]_g$$

wherein R is selected from the group consisting of hydrogen, a $C_{10}$–$C_{22}$ fatty alkoxide chain, ethylenediamine and combinations thereof;
a, b, c and d are independently selected integers ranging from 0 to 200 with proviso that sum of a, b, c and d is at least 5;
e is an integer from 1 to 4;
f is an integer from 0 to 1;
g is an integer from 0 to 4; and
(iv) an effective amount of a fragrance to impart a pleasant odor to said composition, said fragrance including from at most 25% to 0.1% total ester compounds by weight of said fragrance.

DETAILED DESCRIPTION OF THE INVENTION

Now it has been discovered that certain types of fragrance components adversely effect clarity of soap-based cosmetic sticks. Chief among the undesirable components are the category of ester compounds. Normally, fragrances or perfumes comprise mixtures containing volatile organic compounds of different functionalities among which more than often esters are predominant. Consequently, major reconstitution of fragrances has been found necessary for maintenance of stick clarity.

Although not wishing to be bound by any theory, studies pursuant to this invention have suggested the problem may be traced to hydrolysis of the ester compounds. This leads to an acid-base interaction with soap to generate stearic acid. Opacity is known to occur in the presence of sufficient quantities of stearic acid. Loss of long-term clarity is, therefore, believed caused by the formation of free fatty acid from shifts in the equilibrium of the soap. Primary and sterically non-hindered secondary esters are particularly prone toward degrading clarity. Tertiary and sterically hindered secondary esters have proved less detrimental to the formulations.

According to the present invention it is, therefore, desirable to limit the quantity of ester compounds within the fragrance to no more than 25%, preferably no more than 20%, optimally between about 1 and 18% by weight of the total fragrance.

Some level of ester may be necessary to achieve desirable olefactory requirements. Under such circumstances, esters that may be employed include the tertiary and sterically hindered secondary esters. Illustrative of these categories are tertiary esters such as linalyl acetate, dihydro myrcenyl acetate, cedryl acetate and dimethyl benzyl carbinyl acetate. Illustrative of sterically hindered secondary esters are Verdox (ex International Flavors and Fragrances) which is a 2-t-butyl cyclohexyl acetate and $C_8$–$C_{20}$ fatty acid- isopropyl esters such as isopropyl myristate. Sterically hindered secondary esters include those having at least two $C_1$–$C_{40}$ alkyl groups on a carbon situated alpha to the carbinol forming the ester.

Aldehydes are a second, albeit less detrimental, category of fragrance component whose presence should be carefully circumscribed. Again, not to be bound by any theory, there are suggestions from experiments of this invention that certain types of aldehydes are prone to oxidation leading to the corresponding acid; these acids may then have a tendency to effect opacification.

Problems with aldehydes may be minimized by careful selection of these components. Clarity loss may be minimized by use of aldehydes selected from the group consisting of ring substituted and unsubstituted aromatic aldehydes, $C_7$–$C_{20}$ acyclic saturated and unsaturated aliphatic aldehydes, $C_7$–$C_{20}$ cyclic saturated and unsaturated aliphatic aldehydes and combinations thereof. Illustrative of the ring substituted and unsubstituted aromatic aldehydes are cinnamaldehydes, dihydrocinnamaldehydes and vanillin (3-methoxy-4-hydroxybenzaldehyde). Representative of the $C_7$–$C_{20}$ acyclic and cyclic aliphatic aldehydes are heptaldehyde and dodecaldehyde. Levels of aldehyde may range from about 0.1 to about 20% of the fragrance.

Esters which may be suitable for fragrances of this invention are defined as having at least 35% transmittance, preferably at least 60%, when incorporated into an at least 5% aqueous sodium stearate gel stick which has been aged at 100° F. for at least 10 days. Light transmittance is measured in the range 400 to 900 nm through a sample 1 cm thick. Transmittance is measured by placing a stick sample of the required thickness into the light beam path of a UV VIS spectrophotometer.

Aldehydes which may be suitable for fragrances of this invention are defined as having a transmittance of at least 35%, preferably at least 60%, when incorporated into at least 5% aqueous sodium stearate gel stick held at 120° F. for at least 1 month. Light transmittance is measured in the same range and under the same conditions as defined for the ester components.

Total fragrance levels of the present invention may vary from about 0.5 to about 5% by weight of the composition. Preferably total fragrance will vary from about 0.8 to about 3%, optimally between about 1 and 2% by weight.

Although any type of fragrance may be suitable for compositions of the present invention, it is especially preferred to utilize a deoperfume. These perfumes have deodorant properties and have been described by Hooper et al in U.S. Pat. Nos. 4,579,677; 4,322,308; 4,304,679; 4,289,641; 4,288,341; 4,292,192 and by Hagemann et al in U.S. Pat. No. 4,663,068. These patents are herein incorporated by reference. A deoperfume normally will comprise components having a lipoxidase-inhibiting capacity of at least 50% or a Raoult Variance Ratio of at least 1.1, the components being classed into six classes consisting of:

Class 1: phenolic substances
Class 2: essential oils, extracts, resins and synthetic oils
Class 3: aldehydes and ketones
Class 4: polycyclic compounds
Class 5: esters
Class 6: alcohols provided that where a component can be classified into more than one class it is placed in the lower or lowest numbered class; said components being selected so that:
 (a) the deodorant composition contains at least five components of which at least one must be selected from each of class 1, class 2 and class 4;
 (b) the deodorant composition contains components from at least 4 of the 6 classes; and
 (c) any component present in the deodorant composition at a concentration of less than 0.5% by weight of the composition is eliminated from the requirements of (a) and (b).

Deoperfumes will preferably also meet the Deodorant Value Test having a deodorant value of from 0.5 to 3.5.

Clear sticks of the present invention will include a polyhydric alcohol containing from 2 to 6 hydroxyl groups, preferably 2 to 3 hydroxyl groups. The alcohol may also contain from 2 to 6 carbon atoms, preferably 2 to 3 carbon atoms. Suitable polyhydric alcohols include ethylene glycol, propylene glycol, trimethylene glycol, glycerin and sorbitol. Most preferred is propylene glycol. Amounts of the polyhydric alcohol may range from about 10 to about 90%, preferably from about 40 to about 70%, optimally between about 50 and about 65% by weight of the composition.

Another component of compositions of the present invention will be that of a soap. The soap will be derived from $C_{12}$–$C_{22}$, preferably $C_{16}$–$C_{18}$, carbon atom fatty acids in the form of a sodium, potassium or alkanolammonium salt.

Soaps will generally comprise from about 1 to about 40%, preferably from about 3 to about 15%, optimally between about 4 and about 10% by weight of the composition.

Fatty acids which form the soap may include myristic, palmitic, stearic, oleic, linoleic, linolinic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed, rosin acids and greases. Preferred fatty acid soaps are sodium stearate, sodium palmitate, potassium stearate, potassium palmitate, sodium myristate, aluminum monostearate and mixtures thereof.

Compositions of the present invention will also contain an alkoxylate copolymer of the general structure:

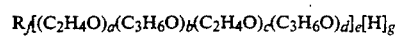

wherein R is selected from the group consisting of hydrogen, a $C_{10}$–$C_{22}$ fatty alkoxide chain, ethylenediamine and combinations thereof;

a, b, c and d are independently selected integers ranging from 0 to 200 with proviso that sum of a, b, c and d is at least 5;

e is an integer from 1 to 4;

f is an integer from 0 to 1; and g is an integer from 0 to 4.

When e and f are 1 and 0, respectively, the structure described is a poly(ethylene oxide)(propylene oxide)-(ethylene oxide) copolymer. Typical of this substance are a series of products from the BASF Corporation sold under the Pluronic trademark. For purposes of this invention, copolymers of this type will have an average molecular weight ranging from about 5000 to about 50,000, preferably between about 6,000 and 15,000. Melt/pour points of these materials should be at least 30° C., preferably at least 50° C., and optimally at least 55° C. Illustrative commercially available products are Pluronic F127® and Pluronic F108®.

When f is 1 and R is ethylenediamine, the general structure defines a tetra-functional block copolymer that may be in terms of species structures (1) and (2) as follows:

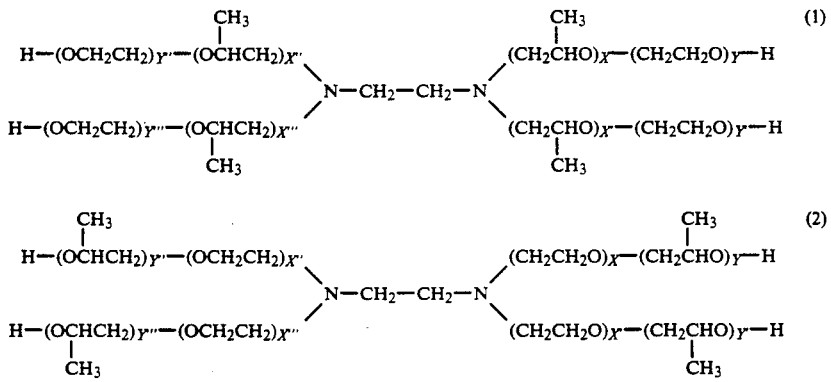

wherein X, X', X'', X''', Y, Y', Y'', Y''' are integers such that the average molecular weight of the copolymer ranges from about 1,500 to 100,000. Preferably, the average molecular weight should range from about 5,000 up to about 50,000, optimally between about 15,000 to about 30,000. Additionally, the copolymers are characterized by having an HLB of at least 12, preferably between 18 and 23, optimally above 24. Best results are obtained when the copolymer has a melt/pour point of at least 30° C., preferably greater than 40° C., optimally greater than 50° C. These structurants are commercially available from the BASF Corporation sold under the trademark, Tetronic®. Especially suitable are Tetronic 1107, Tetronic 1307 and Tetronic 1508.

When f is 1 and R is a $C_{10}$–$C_{22}$ fatty alkoxide (i.e. deprotonated fatty alcohol), the structure described is an ethoxylated and/or propoxylated fatty alcohol copolymer. Illustrative substances are PPG-5-Ceteth 20, PPG-3-Myreth-3 and PEG-20-Laurate. These substances are named with the designation given by the Cosmetic Toiletry and Fragrance Association (CTFA). Advantageously, the extent of total alkoxylation will range anywhere from about 5 to about 95, preferably between about 10 and 80 moles of total alkoxylation per mole of each fatty alkoxide.

Amounts of the copolymer structurant will range anywhere from about 1 to about 40% by weight. Preferably the amount will range from about 2 to 20%, optimally between about 3 and 10% by weight.

A clarifying agent for maintaining clarity of the stick is a further advantageous component of the present invention. This agent will be a basic amine and preferably selected from amino alkanols having from 2 to 6 hydroxyl groups. These alkanols may include anywhere from about 3 to 18 carbon atoms and have molecular weights less than 1,000. Particularly effective are the propanol amines. Illustrative of this category is tetra(-hydroxypropyl) diamine available from the BASF Corporation under the trademark, Quadrol®. Even more preferred is 2-amino-2-methylpropan-1-ol available from the Angus Chemical Company under the trademark, AMP®. Also suitable are 2-amino-2-ethyl-1,3-propanediol available from the Angus Chemical Company under the trademark, AMPD® and 2-amino-2-hydroxymethyl-1,3-propanediol (generically referred to as Tromethamine) available from the Sigma Chemical Company.

The basic amine of the invention will be present in amounts ranging from about 0.1 to about 20%, preferably from about 0.5 to about 5%, optimally between about 1 and 3% by weight.

Skin treatment active agents may also be included within the stick compositions. These agents may range in concentration anywhere from about 0.01 to about 30%, preferably from about 0.1 to about 10%, optimally between about 0.5 and 2% by weight of the composition. Within this category are included bacteriostats, fungistats, sunscreens or ultraviolet absorbers, analgesics, anti-skin wrinkle agents, colorants, astringents and antioxidants.

When the product is a deodorant stick, the active ingredient will be a bacteriostat which includes 2,2'-methylenebis(3,4,6-trichlorophenol), 2,4,4'-trichloro-2'-hydroxy(diphenyl ether), zinc phenolsulfonate, 2,2'-thiobis(4,6-dichlorophenol), p-chloro-m-xylenol, dichloro-m-xylenol and the like. Most preferred is 2,4,4'-trichloro-2'-hydroxy(diphenyl ether), which is generically known as triclosan and available from the Ciba-Geigy Corporation under the trademark, Irgasan DP-300®. When triclosan is utilized it will be present in a range from about 0.05 to about 0.9%, preferably from about 0.1 to about 0.5% by weight of the composition. Other types of bacteriostats include sodium N-lauroyl sarcosine, sodium N-palmitoyl sarcosine, lauroyl sarcosine, N-myristoyl glycine, potassium N-lauroyl sarcosine and aluminum chlorhydroxy lactate (sold by Reheis Chemical Company under trademark of Chloracel).

When the product is a sunscreen composition, the active ingredient may include an ultraviolet absorber such as p-aminobenzoic acid, its salts, or its esters, as well as N-substituted derivatives such as p-(dimethylamino) benzoic acid, an anthranilate, a salicylate, esters of cinnamic acid, dihydroxycinnamic acid or trihydroxycinnamic acid, diphenyl-butadiene, stilbene, a napthol sulfonate, a coumarin derivative, a quinine salt, a quinoline derivative, hydroquinone, tannic acid, zinc oxide, polyethylene particles, titanium dioxide particles, iron oxide particles, dioxybenzone and oxybenzone. Amounts of the ultraviolet absorber may range from about 0.5 to about 5%, preferably from about 1 to 4% by weight of the total composition.

When the composition is a makeup stick in which a solid pigment is to be applied as a rouge, lipstick, eyeshadow or eyeliner, the active ingredient may include titanium dioxide, zinc oxide, iron oxide, aluminum lake, barium lake, calcium lake, strontium lake, tetrabromofluorescein, tetrabromotetrachlorofluorescein, dibromofluorescein and the like. Amounts of the pigment may range from about 1 to about 10%, preferably from about 3 to about 8% by weight of the total composition.

When the product is an anti-skin wrinkle composition, the active ingredient may include ceramides, 2-hydroxyoctanoic acid, retinoic acid, retinol, esters of retinol and retinoic acid, and mixtures thereof. Amounts of the anti-skin wrinkle active ingredient may range from as little as 0.0001 to about 5%, preferably between about 0.001 and about 1% by weight of the composition.

Water is an important component of the compositions of the present invention. Water will generally be present in amounts ranging from about 10 to about 60%, preferably from about 15 to about 40%, optimally between about 25 and 30% by weight.

A variety of optional components may also be present in the compositions of this invention. These optional ingredients may include an emollient. Typical emollients that may be employed include fatty ethers, fatty alcohols and low molecular weight silicone fluids. Specific emollient examples include cetyl alcohol, stearyl alcohol, dimethicone copolyol, cyclomethicone, dimethicone, alkoxylated sugar derivatives such as alkyl polyglycosides and combinations thereof. Amounts of the emollient may range anywhere from about 1 to about 40%, preferably from about 5 to about 25% by weight.

The term "clear" as used in this specification is intended to connote its usual dictionary definition. Thus, a clear cosmetic stick, like glass, allows for ready viewing of objects behind it. By contrast, a transluscent cosmetic stick, although allowing light to pass through, causes the light to be so scattered that it will be impossible to clearly identify objects behind the transluscent stick.

The following examples will more fully illustrate embodiments of this invention. All parts, percentages and proportions referred to herein and in the appended claims are by weight unless otherwise indicated.

EXAMPLE 1

Fragrance compounds were formulated into the base formula as outlined under Table I and then cast into sticks.

TABLE I

| Base Formula | |
|---|---|
| Ingredients | (Wt. %) |
| Propylene Glycol | 63.15 |
| Deionized Water | 27.05 |
| Sodium Stearate | 5.50 |
| Tetronic 1307 | 3.00 |
| Irgasan DP-300 | 0.30 |
| Fragrance | 1.00 |

Each of the above sticks were evaluated for light transmittance and then placed in an oven for accelerated aging studies at temperatures of 70° F., 100° F., 110° F., and 120° F. Results of these experiments are reported in Table II.

TABLE II

| | One-Month Storage | | | | |
|---|---|---|---|---|---|
| Fragrance Compound | Initial Trans(%) | 70° | 100° | 110° | 120° |
| Benzaldehyde | 60 | 18 | 72 | 59 | 15 |
| Hydroxycitronellal | 84 | 75 | 68 | 67 | 46 |
| Ligustral (cyclic aldehyde) | 85 | 75 | 58 | 10 | 0 |
| Lyral (cyclic aldehyde) | 87 | 77 | 76 | 70 | 4 |
| Hexylcinnamic aldehyde | 80 | 77 | 80 | 72 | 73 |
| Dihydromyrcenol (tertiary alcohol) | 88 | 78 | 77 | 75 | 67 |
| Linalyl acetate | 86 | 82 | 62 | 0 | 0 |
| Amyl salicylate | 80 | 35 | 3 | 0 | 0 |
| Benzyl acetate | 85 | 0 | 0 | 0 | 0 |
| Isopropyl myristate | 77 | 69 | 79 | 74 | 71 |
| Geranyl acetate | 86 | 39 | 3 | 0 | 0 |
| Amyl allyl glycolate | 25 | 0 | 0 | 0 | 0 |
| Acetyl tributyl citrate | 87 | 0 | 0 | 0 | 0 |
| Phenyl ethyl alcohol | 86 | 75 | 83 | 77 | 48 |
| Acetyl cedrene (ketone) | 82 | 77 | 83 | 78 | 67 |
| Cedarwood | 80 | 73 | 82 | 74 | 40 |

From Table II it is evident that even at 100° F. storage, primary esters such as amyl salicylate, benzyl salicylate, amyl allyl glycolate and acetyl tributyl citrate cause the stick to opacify. On the other hand, tertiary esters such as linalyl acetate and secondary esters such as isopropyl myristate maintain clarity. Further examples of this trend are illustrated in the shorter, 11-day storage test, Table III.

TABLE III

| | 11-Day Storage | | | | |
|---|---|---|---|---|---|
| Fragrance Compound | Initial Trans(%) | 70° | 100° | 110° | 120° |
| Phenyl ethyl acetate | 89 | 85 | 0 | 0 | 0 |
| Cedryl acetate | 85 | 85 | 48 | 83 | 80 |
| Tangerinol | 87 | 42 | 0 | 0 | 0 |
| Verdox (2-t-butylcyclohexyl acetate) | 87 | 65 | 88 | 84 | 76 |
| Geranyl butyrate | 89 | 80 | 25 | 77 | 12 |
| Dimethyl benzyl carbinyl acetate | 88 | 86 | 62 | 53 | 54 |
| Benzyl acetate | 89 | 42 | 0 | 0 | 0 |
| Geranyl propionate | 87 | 85 | 80 | 87 | 5 |
| Myrcenyl acetate | 89 | 87 | 84 | 79 | 80 |
| Geranyl acetate | 90 | 88 | 11 | 5 | 0 |

EXAMPLE 2

A series of fragrance compositions were formulated into the base stick outlined under Example 1. These fragrance compositions are set forth in Table IV.

TABLE IV

Fragrance Compositions

| Ingredients | (Wt. %) | |
|---|---|---|
| QP-18 | A | B |
| Phenyl ethyl alcohol | 13.00 | 13.00 |
| Dihydromyrcenol | 5.00 | 5.00 |
| Linalool | 8.00 | 8.00 |
| Bergamot oil | 5.00 | 5.00 |
| Galaxolide IPM | 10.00 | 10.00 |
| Isolongifolanone | 5.00 | 5.00 |
| alpha-Methyl ionone Iso | 5.00 | 5.00 |
| Lyral (cycloaliphatic aldehyde) | 4.00 | 4.00 |
| Hexyl cinnamic aldehyde ($\alpha$-$\beta$-unsaturated aldehyde) | 6.00 | 6.00 |
| Lynalyl acetate (ester of tertiary alcohol) | 3.00 | — |
| Citronellyl acetate (ester of primary alcohol) | 5.00 | — |
| Phenyl ethyl acetate (ester of primary alcohol) | 6.00 | — |
| Acetyl tributyl citrate | 25.00 | — |
| Carbitol (diethylene glycol monoethyl ether) | — | 39.00 |
| Total Esters = | 39.00% | — |
| Total Aldehydes = | 10.00% | 10.00% |
| QP-15 | | |
| Benzyl salicylate (ester of primary alcohol) | 6.00 | |
| Coumarin | 4.00 | |
| Phenyl ethyl alcohol | 10.00 | |
| Lilial (aryl substituted aldehyde) | 5.00 | |
| alpha-Methyl ionone Iso | 3.00 | |
| Para-t-butyl cyclohexyl acetate (ester of secondary alcohol) | 6.00 | |
| Dihydromyrcenol | 12.00 | |
| Acetyl cedrene | 6.00 | |
| Allyl amyl glycolate (ester of primary alcohol) | 1.00 | |
| Galaxolide IPM | 5.00 | |
| Vanillin | 3.00 | |
| Hexyl cinnamic aldehyde ($\alpha,\beta$-unsaturated aldehyde) | 5.00 | |
| Patchouli oil | 5.00 | |
| Bergamot oil | 10.00 | |
| Citronellol | 10.00 | |
| Carbitol | 7.00 | |
| Total Esters = | 13.0% | |
| Total Aldehydes = | 11.0% | |
| Op-21 | | |
| Phenyl ethyl alcohol | 15.00 | |
| Dihydromyrcenol | 8.00 | |
| alpha-Methyl ionone Iso | 6.00 | |
| Bergamot oil | 5.00 | |
| Benzyl salicylate (ester of primary alcohol) | 3.00 | |
| Styrallyl acetate (ester of primary alcohol) | 3.00 | |
| Hedione | 5.00 | |
| Lavindin oil abrialis | 10.00 | |
| Lyral (cycloaliphatic aldehyde) | 1.00 | |
| Pathouly oil | 8.00 | |
| Lemon oil | 10.00 | |
| Galoxolide DEP | 16.00 | |
| Linalool | 5.00 | |
| Acetyl cedrene | 5.00 | |
| Total Esters = | 6.0% | |
| Total Aldehydes = | 1.0% | |
| QP-90 | | |
| Benzyl salicylate (ester of primary alcohol) | 4.00 | |
| Coumarin | 3.00 | |
| Musk ketone | 5.00 | |
| Rosewood oil | 5.00 | |
| Hedione | 6.00 | |
| Lemon oil | 5.00 | |
| Patchouly oil | 4.00 | |
| alpha-Terpineol | 8.00 | |
| Galaxolide IPM | 30.00 | |
| Phenyl ethyl alcohol | 9.00 | |
| Triethyl citrate (ester of primary alcohol) | 14.00 | |
| Lyral (cycloaliphatic aldehyde) | 4.00 | |
| Heliotrpine (substituted aromatic aldehyde) | 1.00 | |
| Hexyl cinnamic aldehyde ($\alpha,\beta$-unsaturated aldehyde) | 2.00 | |

TABLE IV-continued

Fragrance Compositions

| Ingredients | (Wt. %) |
|---|---|
| Total Esters = | 18.0% |
| Total Aldehydes = | 7.0% |

Sticks with each of the above fragrance compositions were evaluated for clarity stability under accelerated aging conditions. Results of these tests are outlined under Table V.

TABLE V

| | One-Month Storage | | | | |
|---|---|---|---|---|---|
| Fragrance Compound | Initial Trans(%) | 70° | 100° | 110° | 120° |
| QP-18-A | 85 | 19 | 0 | 0 | 0 |
| QP-18-B (esters replaced w/carbitol) | 85 | 75 | 82 | 49 | 22 |
| QP-18-C (without esters or carbitol) | 85 | 78 | 79 | 57 | 5 |

Evident from Table V is that removal of ester components from the fragrance composition markedly improved clarity stability. Compare QP-18-A versus the non-ester fragrances, QP-18-B and C.

Similarly by contrast with QP-18-A, fragrance compositions QP-15, QP-21 and QP-90, each formulated at 1% in the clear base formula, did not degrade the stick clarity even after one month storage at 110° F. Levels of total esters/aldehydes for QP-15, QP-21 and Q-90 were 13%/11%, 6%/1% and 18%/7%, respectively. Through maintenance of total ester levels substantially below 39%, there was thus achieved an effective stabilization of clarity.

The foregoing description and examples illustrate selected embodiments of the present invention and in light thereof variations and modifications will be suggested to one skilled in the art, all of which are in the spirit and purview of this invention.

What is claimed is:

1. A clear stick composition comprising:
   (i) from about 10 to about 90% of a polyhydric alcohol having from 2 to 6 carbon atoms and from 2 to 6 hydroxyl groups;
   (ii) from about 1 to about 40% of a soap which is a $C_{12}$–$C_{22}$ fatty acid of a salt selected from the group consisting of sodium, potassium and alkanolammonium salts;
   (iii) from about 1 to about 40% of an alkoxylate copolymer having the following formula:

$$R_f[(C_2H_4O)_a(C_3H_6O)_b(C_2H_4O)_c(C_3H_6O)_d]_e[H]_g$$

wherein R is selected from the group consisting of hydrogen, a $C_{10}$–$C_{22}$ fatty alkoxide chain, ethylenediamine and combinations thereof;
   a, b, c and d are independently selected integers ranging from 0 to 200 with proviso that sum of a, b, c and d is at least 5 and no higher than 95;
   e is an integer from 1 to 4;
   f is an integer from 0 to 1;
   g is an integer from 0 to 4; and
   (iv) an effective amount of a fragrance to impart a pleasant odor to said composition, said fragrance including from 25% down to 0.1% of total ester compounds by weight of said fragrance.

2. The composition according to claim 1, wherein said copolymer is a tetra-functional block copolymer derived from addition of propylene oxide and ethylene oxide to ethylene diamine.

3. The composition according to claim 2, wherein said polymer has a molecular weight of at least 5000.

4. The composition according to claim 1, wherein said copolymer is a block copolymer formed solely of propylene oxide and ethylene oxide.

5. The composition according to claim 1, wherein said copolymer is formed of alternating blocks of poly(ethylene oxide), poly(propylene oxide) and poly(ethylene oxide).

6. The composition according to claim 1, wherein said ester compounds are present in an amount of 20%, down to about 1% by weight of the fragrance.

7. The composition according to claim 1, wherein said fragrance is present in an amount from about 0.5 to about 5% by weight of the total composition.

8. The composition according to claim 1, wherein the only aldehydes present in said fragrance are selected from the group consisting of substituted and unsubstituted aromatic aldehydes, cyclic aliphatic aldehydes, acyclic aliphatic aldehydes and combinations thereof in amounts ranging from about 0.1 to about 20% by weight of fragrance.

9. The composition according to claim 1, wherein only fragrance esters are present that are selected from the group consisting of tertiary esters, sterically hindered secondary esters and combinations thereof.

10. The composition according to claim 9, wherein said sterically hindered secondary esters are isopropyl esters.

11. The composition according to claim 9 wherein said sterically hindered secondary esters have at least two $C_1$-$C_{40}$ alkyl groups alpha to a carbinol forming said esters.

12. The composition according to claim 9, wherein said tertiary esters are selected from the group consisting of linalyl acetate, dihydro myrcenyl acetate, cedryl acetate, dimethyl benzyl carbinyl acetate and combinations thereof.

* * * * *